US009776019B2

(12) United States Patent
Saito et al.

(10) Patent No.: US 9,776,019 B2
(45) Date of Patent: Oct. 3, 2017

(54) PARTICLE BEAM THERAPY SYSTEM

(71) Applicant: HITACHI, LTD., Tokyo (JP)

(72) Inventors: Kazuyoshi Saito, Tokyo (JP); Takuya Nomura, Tokyo (JP); Hideaki Nishiuchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 453 days.

(21) Appl. No.: 14/132,965

(22) Filed: Dec. 18, 2013

(65) Prior Publication Data
US 2014/0187844 A1     Jul. 3, 2014

(30) Foreign Application Priority Data

Dec. 27, 2012  (JP) .................................. 2012-283858

(51) Int. Cl.
*H05H 13/04*     (2006.01)
*H05H 7/10*      (2006.01)
(Continued)

(52) U.S. Cl.
CPC ............. *A61N 5/1077* (2013.01); *H05H 7/10* (2013.01); *H05H 13/04* (2013.01); *A61N 2005/1087* (2013.01); *H05H 2007/004* (2013.01)

(58) Field of Classification Search
CPC ........ A61N 5/1077; H05H 7/10; H05H 13/04; H05H 2007/004
See application file for complete search history.

(56) References Cited

U.S. PATENT DOCUMENTS 5,363,008 A * 11/1994 Hiramoto ............... H05H 13/00
                                                    313/62
7,122,978 B2   10/2006 Nakanishi et al.
(Continued)

FOREIGN PATENT DOCUMENTS

| JP | 2005-332794 A | 12/2005 |
|----|---------------|---------|
| JP | 2008-226740 A | 9/2008  |
| JP | 2009-112483 A | 5/2009  |

OTHER PUBLICATIONS

Iwata et al., "Multiple-energy operation with extended flattops at HIMAC", Nuclear Instruments and Methods in Physics Research, A 624, 2010, pp. 33-38.

(Continued)

*Primary Examiner* — Jason McCormack
*Assistant Examiner* — Sean Luck
(74) *Attorney, Agent, or Firm* — Mattingly & Malur, PC

(57) ABSTRACT

A particle beam therapy system is disclosed which includes: a synchrotron accelerating a charged particle beam injected from a pre-accelerator up to a predetermined energy level before applying a high-frequency voltage to an extraction device to extract the charged particle beam caused to exceed a stability limit; a beam transportation system transporting the charged particle beam extracted from the synchrotron up to a treatment room, and an irradiation device irradiating a patient in the treatment room with the charged particle beam in conformity to the patient's tumor shape. The synchrotron has functionality to accelerate or decelerate the charged particle beam successively to extract the charged particle beam at a plurality of energy levels during an extraction phase of the synchrotron, the beam transportation system further having functionality to block off an unnecessary charged particle beam extracted from the synchrotron during acceleration or deceleration.

4 Claims, 8 Drawing Sheets

(51) Int. Cl.
*A61N 5/10* (2006.01)
*H05H 7/00* (2006.01)

(56) References Cited

U.S. PATENT DOCUMENTS

| | | | | |
|---|---|---|---|---|
| 7,576,342 B2 * | 8/2009 | Hiramoto | ............... | A61N 5/10 |
| | | | | 250/492.21 |
| 8,227,775 B2 | 7/2012 | Saito et al. | | |
| 8,742,699 B2 * | 6/2014 | Umezawa | ............ | G21K 1/093 |
| | | | | 315/500 |
| 2004/0227104 A1 * | 11/2004 | Matsuda | ............... | A61N 5/10 |
| | | | | 250/492.1 |
| 2005/0231138 A1 * | 10/2005 | Nakanishi | ............... | G21K 5/04 |
| | | | | 315/500 |
| 2009/0114852 A1 * | 5/2009 | Saito | ................. | A61N 5/1048 |
| | | | | 250/492.3 |

OTHER PUBLICATIONS

Nishiuchi et al., Unpublished U.S. Appl. No. 13/945,041, filed Jul. 18, 2013,.
Japanese Office Action received in corresponding Japanese Application No. 2012-283858 dated Nov. 17, 2015.

* cited by examiner

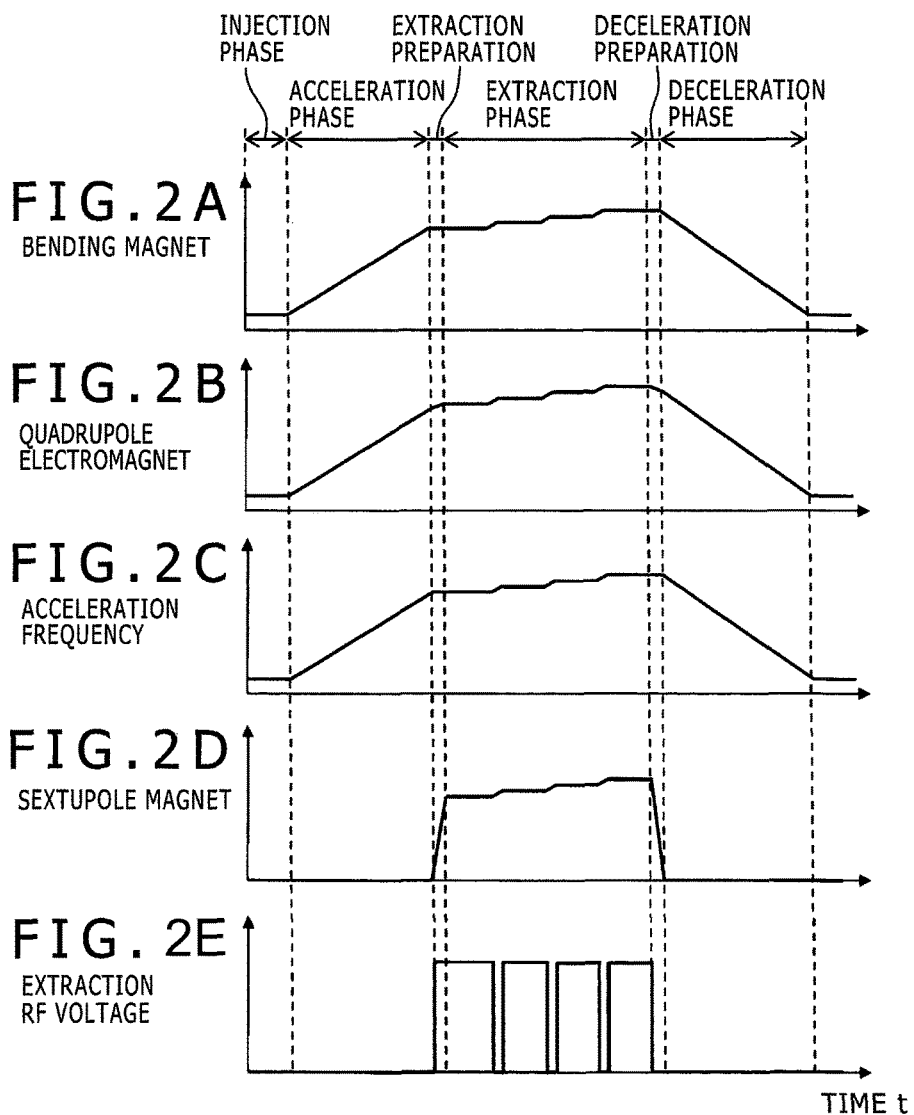

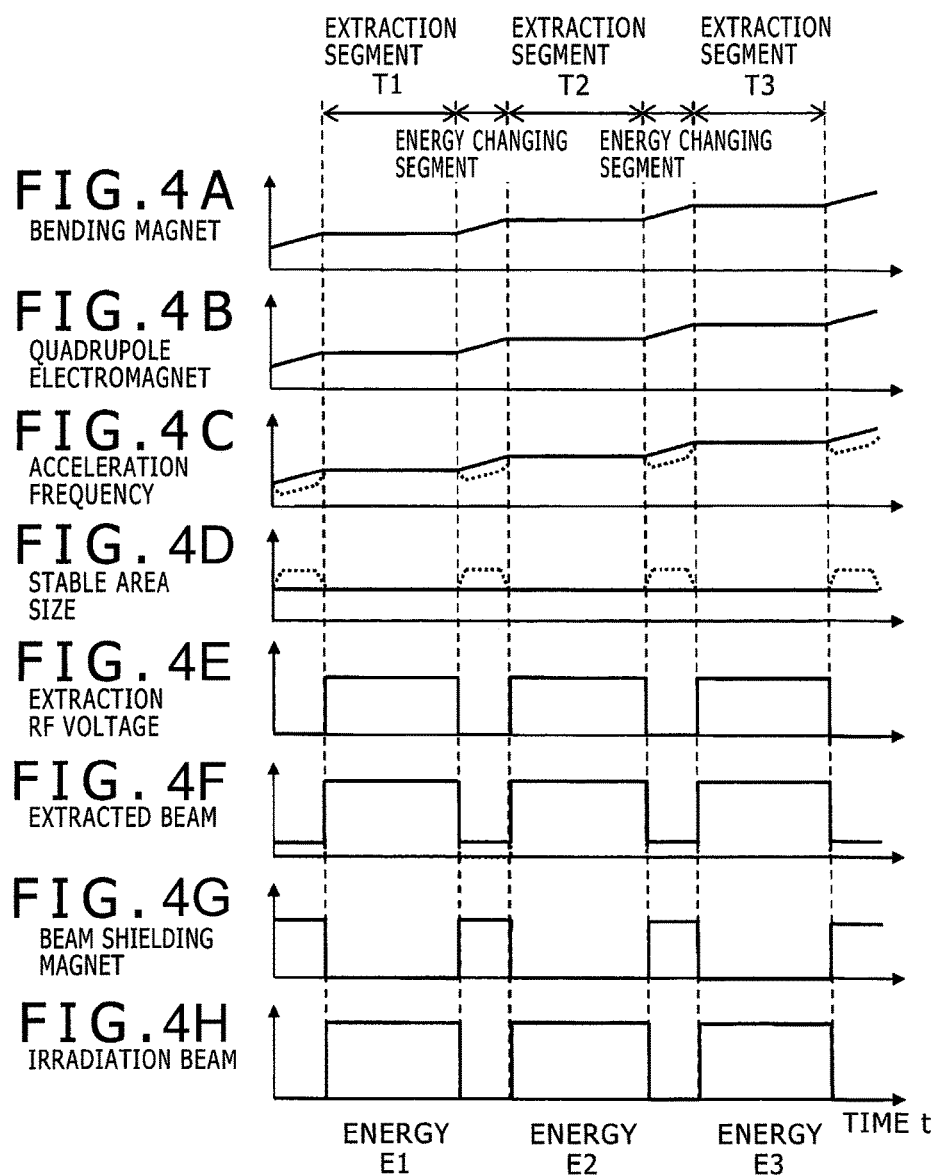

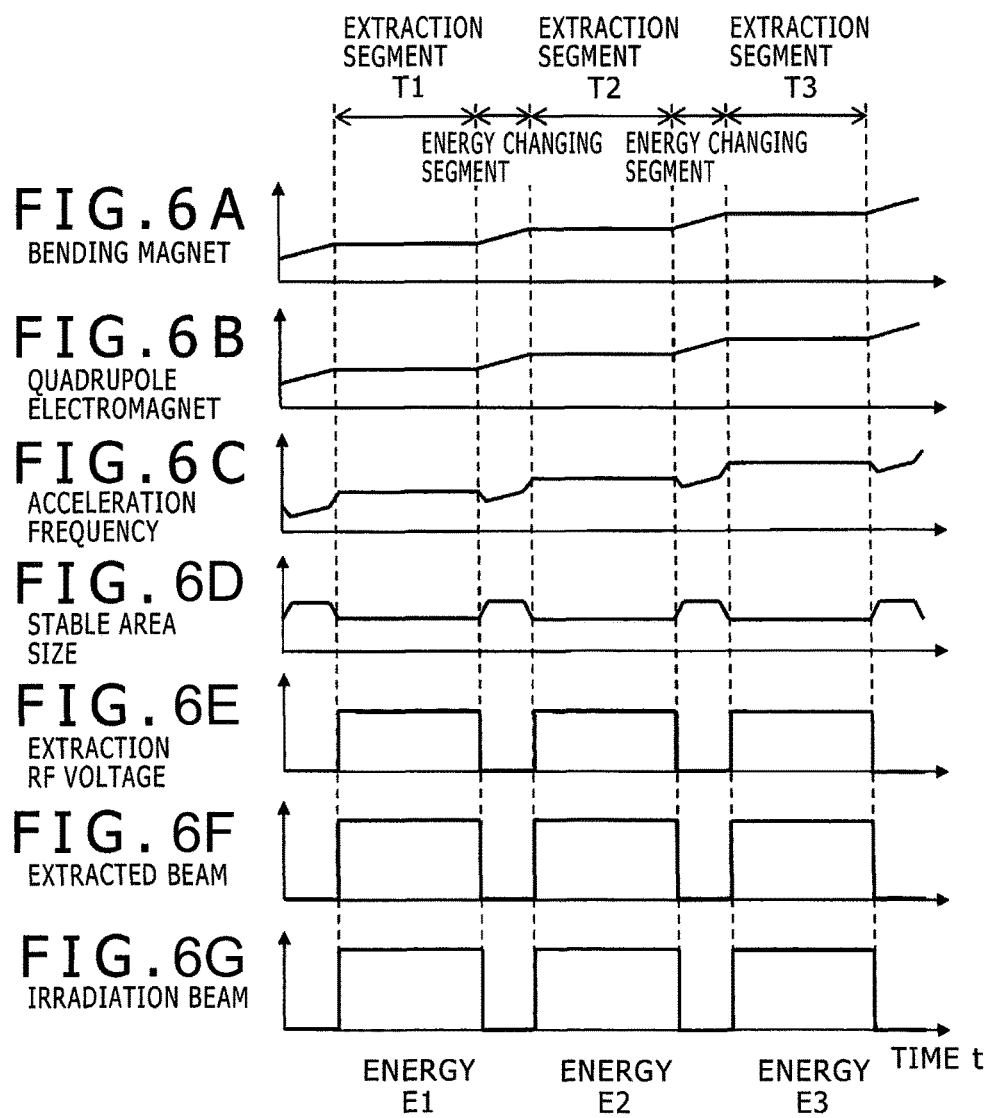

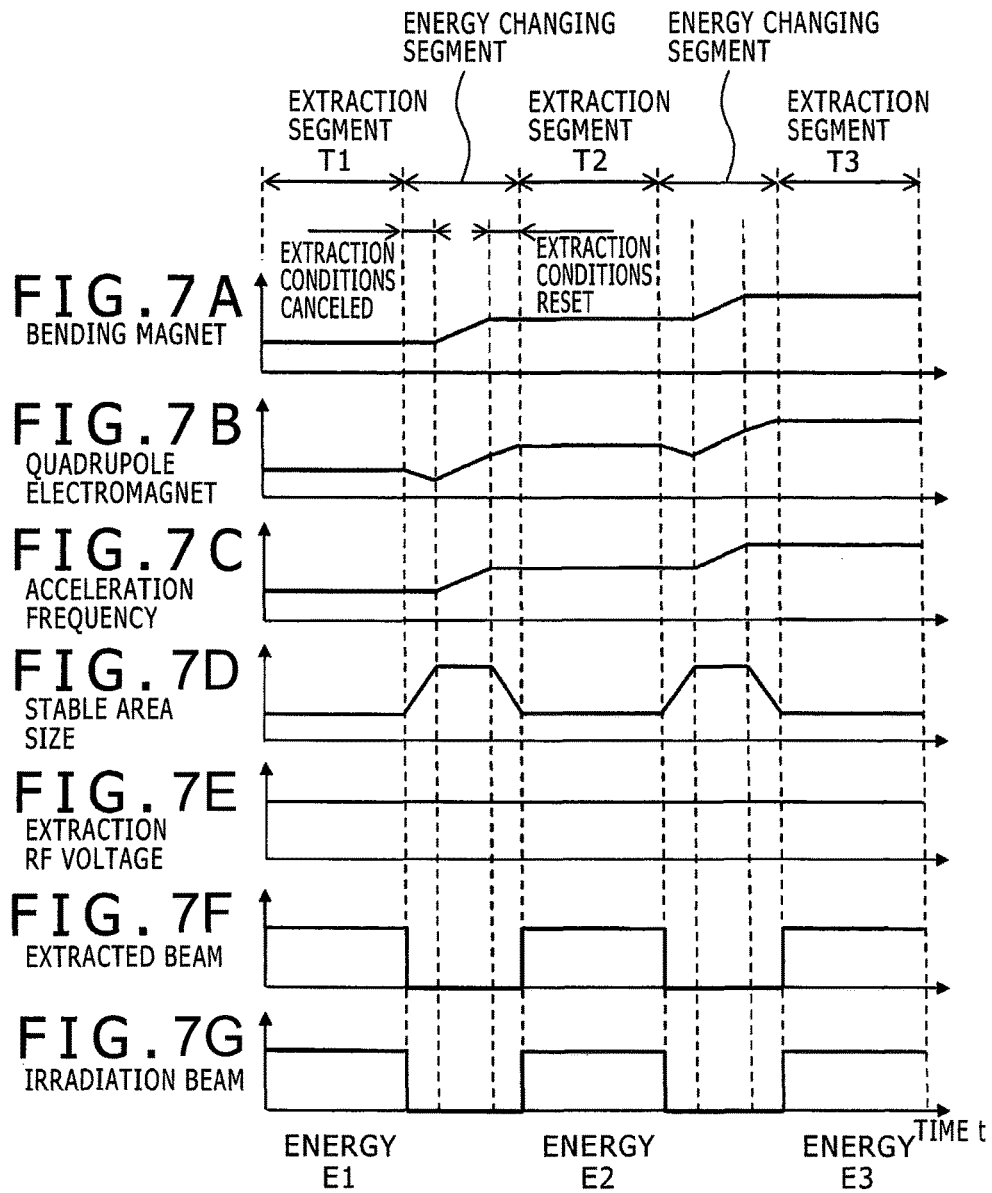

PARTICLE BEAM THERAPY SYSTEM

BACKGROUND OF THE INVENTION

1. Field of the Invention

The present invention relates to a particle beam therapy system capable of highly accurate therapeutic irradiation. More particularly, the invention relates to a particle beam therapy system that uses advanced irradiation technology such as the scanning method capable of highly precise therapeutic irradiation in conformity to a complex target shape.

2. Description of the Related Art

Against the background of an aging society in recent years, attention has been drawn to radiation therapies which, as cancer treatment, are minimally invasive to the body and permit a high quality of life to be maintained after the treatment. One of the most promising of these therapies is the particle beam therapy system that offers good dose concentration on the tumor using a charged particle beam of protons, carbon particles, etc., accelerated by an accelerator. The particle beam therapy system is typically composed of an accelerator such as a synchrotron that accelerates a beam from an ion source close to light speed, a beam transportation system that transports the extracted beam from the accelerator, and an irradiation device that irradiates the patient with the beam in conformity to the position and shape of the tumor.

In applying the beam in conformity to the tumor's shape with the irradiation device of the particle beam therapy system, the scatterer irradiation method is adopted whereby the beam diameter is enlarged using a scatterer before being trimmed to shape by a collimator trimming the beam diameter periphery, or the scanning method is used which involves a small-diameter beam from an accelerator being deflected by magnets to scan the tumor in conformity to its shape. Coming into the mainstream in recent years is the scanning method capable of highly accurate therapeutic irradiation in conformity to a complex target shape. As with the conventional scatterer irradiation method, the scanning method is required to provide a standard nominal value of 2 Gy/min in dose rate for every 1 L of irradiation volume with a view to shortening therapeutic irradiation time.

The scanning method involves dividing a three-dimensional tumor shape into a plurality of layers in the depth direction and further diving each of the layers two-dimensionally to set up a plurality of irradiation spots. In the depth direction, each of the layers is irradiated selectively with a beam at varying energy levels. In each layer, the irradiation beam is moved two-dimensionally for scanning so as to give a predetermined dose to each of the irradiation spots. A method of continuously activating the irradiation beam during movement between irradiation spots is called raster scanning. On the other hand, a method of deactivating the irradiation beam during such movement is called spot scanning. Where a synchrotron is used as the accelerator with any of these scanning methods, a charged particle beam is accelerated to an energy level corresponding to each of the layers in the depth direction of the tumor before the beam is extracted to the beam transportation system. By way of the beam transportation system, the charged particle beam is transported to the irradiation device which in turn applies the transported beam selectively to the layers of the tumor in question.

Conventional methods for operating the synchrotron typically involve accelerating a charged particle beam injected from a pre-accelerator up to a predetermined energy level, extracting the charged particle beam at the energy level in effect upon completion of acceleration, and decelerating the residual beam upon completion of extraction down to the energy level in effect upon beam injection before discarding the beam. That is, the conventional synchrotron simply repeats an operating cycle of injection, acceleration, extraction and deceleration. During the extraction phase of one operating cycle, only the charged particle beam at a single energy level can be extracted. Thus in cases where the irradiation beam at a plurality of energy levels is needed to address a plurality of layers of the tumor in the depth direction with the scanning method, it is necessary to again carry out deceleration, injection and acceleration every time the energy level is changed even if there remains a sufficient orbiting beam in the synchrotron. This poses the problem about prolonged therapeutic irradiation time because of reduced dose rates.

As one solution to the above problem, Japanese Patent No. 4873563 discloses an operation method involving a synchrotron successively accelerating or decelerating the orbiting beam during the extraction phase so as to extract a charged particle beam at a plurality of energy levels. The synchrotron operation method described by the above-cited patent indeed shortens the time required to change energy levels so as to improve dose rates thereby shortening therapeutic irradiation time. However, the disclosed method is not necessarily sufficient to attain the required standard nominal value of 2 Gy/min in dose rate for every 1 L of irradiation volume.

The results of experiments with a synchrotron for carbon-beam treatment realized by implementing the operation method described in the above-cited patent are disclosed in "Multiple-energy operation with extended flattops at HIMAC," Nuclear Instruments and Methods in Physics Research A624 (2010) 33-38. The latter publication describes an operation method whereby the size of a stability limit is enlarged using quadrupole electromagnet prior to acceleration or deceleration of a charged particle beam so as to suppress the extraction of an unnecessary charged particle beam from the synchrotron at the time of acceleration or deceleration for energy level change, the stability limit being again reduced to the original size upon completion of acceleration or deceleration. This method entails the problem about low speed response of the quadrupole electromagnet because of their large inductance values, which prolongs the time required to change energy levels. Although there exists a method involving a synchrotron being separately equipped with dedicated small-inductance quadrupole electromagnet permitting high-speed response, this method can lead to the synchrotron getting larger in size and higher in cost. This is not a realistic option for the synchrotron for proton-beam treatment that must be small in size and low in cost.

SUMMARY OF THE INVENTION

It is therefore an object of the present invention to provide a particle beam therapy system using a synchrotron that extracts a charged particle beam at a plurality of energy levels during an extraction phase by successively accelerating or decelerating an orbiting beam during that phase to change the beam energy, the system being arranged to shorten the time required for the energy change in order to improve dose rates and shorten therapeutic irradiation time with the scanning method. Another object of the present invention is to provide a particle beam therapy system that keeps the synchrotron from getting larger in size and higher in cost.

In achieving the foregoing and other objects of the present invention and according to one aspect thereof, there is provided a particle beam therapy system including: a synchrotron which accelerates a charged particle beam injected from a pre-accelerator up to a predetermined energy level before applying a radio frequency (rf) voltage to an extraction device to extract the charged particle beam caused to exceed a stability limit; a beam transportation system which transports the charged particle beam extracted from the synchrotron up to a treatment room, and an irradiation device which irradiates a patient in the treatment room with the charged particle beam in conformity to the tumor shape of the patient. The synchrotron has functionality to accelerate or decelerate the charged particle beam successively to extract the charged particle beam at a plurality of energy levels during an extraction phase of the synchrotron, the beam transportation system further having functionality to block off an unnecessary charged particle beam extracted from the synchrotron during acceleration or deceleration.

Preferably, during the extraction phase of the synchrotron during which the synchrotron extracts the charged particle beam at a plurality of energy levels by successively accelerating or decelerating the charged particle beam, magnets constituting part of the synchrotron may be controlled to maintain the stability limit substantially constant in size, and the rf voltage applied to the extraction device may be turned off during acceleration or deceleration.

Preferably, upon acceleration or deceleration of the charged particle beam during the extraction phase of the synchrotron, the synchrotron may suppress the extraction of the unnecessary charged particle beam by having an acceleration frequency controlled to enlarge the stability limit in size.

In attaining the foregoing and other objects of the present invention and according to another aspect thereof, there is provided a particle beam therapy system including: a synchrotron which accelerates a charged particle beam injected from a pre-accelerator up to a predetermined energy level before applying an rf voltage to an extraction device to extract the charged particle beam caused to exceed a stability limit; a beam transportation system which transports the charged particle beam extracted from the synchrotron up to a treatment room, and an irradiation device which irradiates a patient in the treatment room with the charged particle beam in conformity to the tumor shape of the patient. The synchrotron has functionality to accelerate or decelerate the charged particle beam successively to extract the charged particle beam at a plurality of energy levels during an extraction phase of the synchrotron, the synchrotron further having functionality to suppress the extraction of an unnecessary charged particle beam by having an acceleration frequency controlled to enlarge the stability limit in size during acceleration or deceleration.

According to this invention, it is possible to improve dose rates by shortening the time required to change energy levels during the extraction phase and by raising the efficiency in beam utilization while keeping the system from getting larger in size and higher in cost, whereby therapeutic irradiation time with the scanning method can be shortened.

BRIEF DESCRIPTION OF THE DRAWINGS

Further objects and advantages of the present invention will become apparent upon a reading of the following description and appended drawings in which:

FIGS. 2A through 2E are sequence diagrams outlining an operation sequence of a synchrotron used by the particle beam therapy system as the first embodiment of the invention;

FIGS. 4A through 4H are sequence diagrams showing details of the operation sequence and time changes in operation parameters with the particle beam therapy system as the first and a second embodiment of the invention during the extraction phase of the synchrotron, with broken lines in the diagrams corresponding to the second embodiment and indicating differences from the first embodiment;

FIGS. 6A through 6G are sequence diagrams showing detailed operation sequences and time changes in operation parameters with the particle beam therapy system as the third embodiment during the extraction phase of its synchrotron;

FIGS. 7A through 7G are sequence diagrams showing detailed operation sequences and time changes in operation parameters with a conventional particle beam therapy system during the extraction phase of its synchrotron.

DESCRIPTION OF THE PREFERRED EMBODIMENTS

First Embodiment

Figure 1:
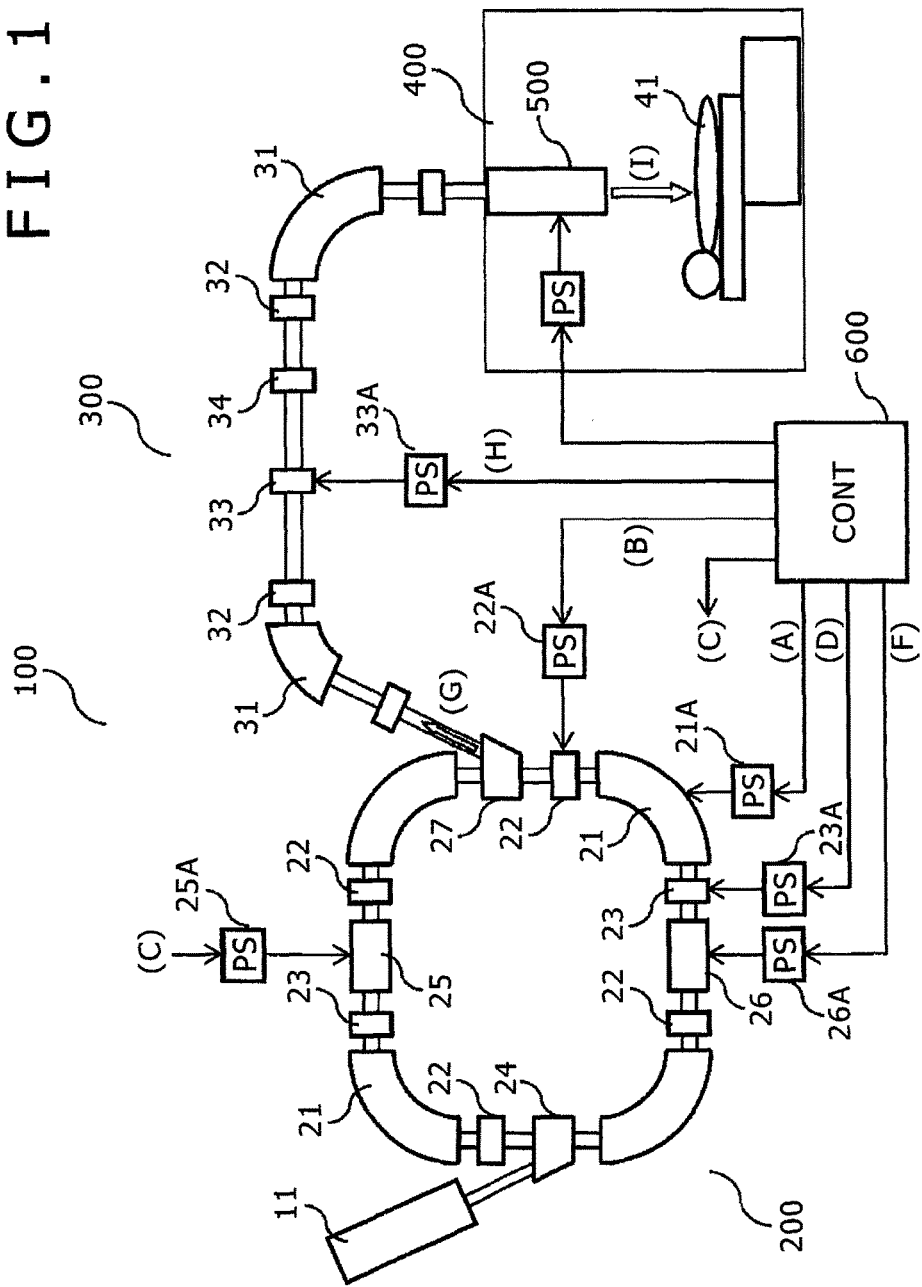
FIG. 1 is a schematic view showing a configuration of a particle beam therapy system as a first embodiment of the present invention.

The configuration and the operation of a particle beam therapy system 100 practiced as the first embodiment of the present invention are explained below with reference to FIGS. 1 through 4H. Explained first with reference to FIG. 1 is an overall configuration of the particle beam therapy system 100 as the first embodiment.

The particle beam therapy system 100 includes a synchrotron 200 that accelerates to a predetermined energy level a charged particle beam pre-accelerated by a pre-accelerator 11 such as a linac before extracting the accelerated charged particle beam, a beam transportation system 300 that transports the charged particle beam extracted from the synchrotron 200 up to a treatment room 400, an irradiation device 500 that irradiates a patient 41 in the treatment room 400 with the charged particle beam in conformity to the patient's tumor shape, and a control apparatus 600.

The control apparatus 600 controls the devices constituting the pre-accelerator 11, synchrotron 200, beam transportation system 300, and irradiation device 500 and their power supplies, thereby controlling and monitoring the synchrotron 200 in each phase of its operation sequence as well as controlling and monitoring the beam irradiation of the irradiation device 500. It should be noted that FIG. 1 depicts only the relations between the devices closely related to this embodiment and their power supplies, using command signals (A) through (D), (F) and (H) transmitted from the control apparatus 600.

The synchrotron 200 includes an injection device 24 that injects the charged particle beam pre-accelerated by the pre-accelerator 11, bending magnets 21 and an excitation power supply 21A for bending the charged particle beam and causing the beam to orbit on a predetermined orbit, converging/diverging type quadrupole electromagnet 22 and an excitation power supply 22A for providing convergent force in the horizontal and vertical directions to keep the charged particle beam from spreading, an accelerating cavity 25 and an excitation rf power supply 25A for accelerating the charged particle beam to a predetermined energy level using an rf voltage, sextuple electromagnet 23 and an excitation power supply 23A for forming a stability limit with regard to the oscillation amplitude of the orbiting charged particle beam, an extraction device 26 and an excitation rf power supply 26A for increasing the oscillation amplitude of the charged particle beam using an rf voltage applied across electrodes so that the charged particle beam is caused to exceed the stability limit and extracted to the outside, and an extraction bending device 27 for bending the charged particle beam to be extracted.

Explained next with reference to FIGS. 2A through 2E is an overall operation sequence of the synchrotron 200 used by the particle beam therapy system of this embodiment. In each of FIGS. 2A through 2E, the horizontal axis denotes time t. The vertical axis in FIG. 2A represents an excitation current supplied from the excitation power supply 21A to the bending magnet 21 in response to a command signal transmitted from the control apparatus 600 to the excitation power supply 21A of the bending magnet 21. The vertical axis in FIG. 2B represents an excitation current supplied from the excitation power supply 22A to the quadrupole electromagnet 22 in response to a command signal transmitted from the control apparatus 600 to the excitation power supply 22A of the quadrupole electromagnet 22. The vertical axis in FIG. 2C represents the frequency of an rf voltage supplied from the rf power supply 25A to the accelerating cavity 25 in response to a command signal transmitted from the control apparatus 600 to the rf power supply 25A of the accelerating cavity 25. The vertical axis in FIG. 2D represents an excitation current supplied from the excitation power supply 23A to the sextuple electromagnet 23 in response to a command signal transmitted from the control apparatus 600 to the excitation power supply 23A of the sextuple electromagnet 23. The vertical axis in FIG. 2E represents an amplitude value of an rf voltage supplied from the rf power supply 26A to the extraction device 26 in response to a command signal transmitted from the control apparatus 600 to the rf power supply 26A of the extraction device 26.

The synchrotron 200 repeats the operating cycle of injection, acceleration, extraction and deceleration, as shown in FIGS. 2A through 2E. During the injection phase, the charged particle beam pre-accelerated by the pre-accelerator 11 is injected and stored. The control apparatus 600 sets excitation currents of the bending magnets 21 and quadrupole electromagnet 22 in such a manner that the charged particle beam at a low energy level will orbit stably on a predetermined orbit. During the acceleration phase, the injected beam is captured in a bunch and accelerated with an rf applied to the accelerating cavity 25. The control apparatus 600 raises the frequency of the rf voltage in keeping with an orbiting frequency of the charged particle beam that rises as acceleration proceeds. Also, the control apparatus 600 performs control to raise the excitation currents of the bending magnets 21 and quadrupole electromagnet 22 as the acceleration of the charged particle beam proceeds so that the currently accelerated charged particle beam may stably orbit on a predetermined orbit. During an extraction preparation phase, the control apparatus 600 excites the sextuple electromagnet 23 to form the stability limit with regard to the oscillation amplitude of the orbiting charged particle beam, while also changing the excitation current of the quadrupole electromagnet 22 from the value in effect upon completion of acceleration to a value optimal for beam extraction. This is called the setting of the extraction conditions. Also, the control apparatus 600 raises the oscillation amplitude of the orbiting beam close to the stability limit with the rf voltage applied to the extraction device 26. During the extraction phase, the control apparatus 600 further increases the oscillation amplitude of the orbiting beam in such a manner that the beam is caused to exceed the stability limit and extracted. The synchrotron 200 of this embodiment accelerates successively the orbiting beam during the extraction phase so that the charged particle beam is extracted at a plurality of energy levels during the extraction phase of each operating cycle. The operation sequence during the extraction phase will be discussed later in detail in comparison with conventional techniques. During a deceleration preparation phase, the control apparatus 600 stops excitation of the sextuple electromagnet 23 to let the stability limit disappear, while also changing the excitation current of the quadrupole electromagnet 22 to a value optimal for starting deceleration. This is called the cancellation of the extraction conditions. The deceleration phase is the reverse of the acceleration phase. During this phase, the residual beam in effect upon completion of the extraction phase is decelerated down to the energy level in effect upon injection and discarded.

Figure 8A:
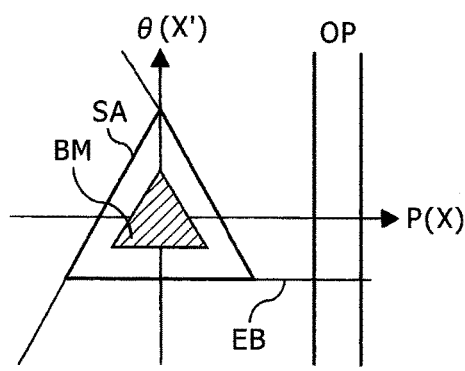
FIGS. 8A, 8B and 8C are explanation drawings for explaining a beam extraction method of a synchrotron by showing how an orbiting charged particle beam in the synchrotron behaves in horizontal topological spaces associated with extraction, FIG. 8A showing a topological space in effect after acceleration and before the start of the extraction phase (i.e., during extraction preparation phase), FIG. 8B indicating a topological space in effect when the size of the stability limit is kept optimal for beam extraction during the extraction phase, FIG. 8C depicting a topological space in effect when the stability limit is enlarged in size to suppress beam extraction upon energy level change during the extraction phase.
Figure 8B:
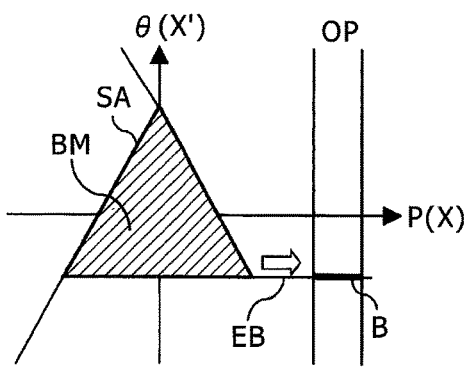
Figure 8C:
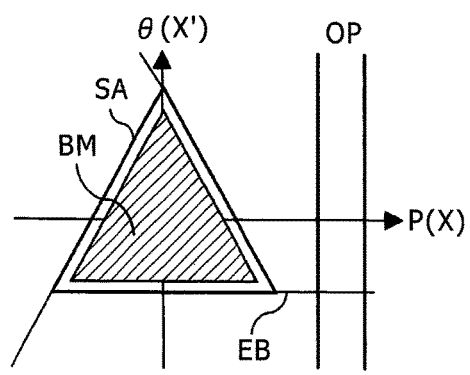

Explained below with reference to FIGS. 8A through 8C is the principle of the method for extracting the charged particle beam from the synchrotron of this embodiment. FIGS. 8A through 8C show, in a horizontal topological space associated with extraction, the state of the charged particle beam orbiting in the synchrotron. The particles constituting the charged particle beam orbit as an orbiting beam BM vibrating in a manner centering on a design orbit. The horizontal axis denotes deviations (position P) from the design orbit, and the vertical axis represents gradients (angle θ) relative to the design orbit. FIG. 8A shows a topological space in effect after acceleration and before the start of the extraction phase (i.e., during extraction preparation phase). FIG. 8B indicates a topological space in effect when the size of the stability limit is kept optimal for beam extraction during the extraction phase.

During the extraction preparation phase, exciting the sextuple electromagnet 23 shown in FIG. 1 forms a triangular stability limit (of which the inside is defined as the stable area SA) in the topological space as indicated in FIG. 8A. The size of the stability limit (stable area SA) is determined by the excitation currents of the quadrupole electromagnet 22 and sextuple electromagnet 23. The particles in the stable area continue to orbit stably in the synchrotron. At this point, applying an rf voltage to the extraction device 26 shown in FIG. 1 expands the oscillation amplitude of the orbiting beam BM close to the stability limit. And as shown in FIG. 8B, the particles overflowing the stability limit during the extraction phase abruptly grow in oscillation amplitude along an extraction branch EB and eventually fly into an opening OP of the extraction bending device 27. The particles are then extracted from the synchrotron as an extracted beam B.

The beam transportation system 300 is explained below by again referring to FIG. 1. The beam transportation system 300 includes bending magnets 31 that bend the extracted beam coming from the synchrotron with magnetic fields to let the beam reach the irradiation device 500 inside the treatment room 400 along a predetermined design orbit, converging/diverging type quadrupole electromagnet 32 that provide convergent force in the horizontal and vertical directions to keep the charged particle beam from spreading while being transported, a beam shielding magnet 33 and an excitation power supply 33A for turning on and off the supply of the charged particle beam to the irradiation device 500, and a beam dump 34 that discards the beam blocked by the beam shielding magnet 33.

Incidentally, the beam shielding magnet 33 may operate on one of two methods: bending the unnecessary beam with a bipolar magnetic field stemming from excitation and discarding the beam through the beam dump 34, or supplying the irradiation device 500 only with the beam bent by the bipolar magnetic field derived from excitation. The former method is characterized by the ease of adjusting the beam transportation system. The latter method offers higher safety because it reliably blocks the supply of the charged particle beam to the irradiation device upon device failure. Whereas any of these methods can be adopted, the former method is used by this embodiment in describing its workings hereunder.

Figure 3A:
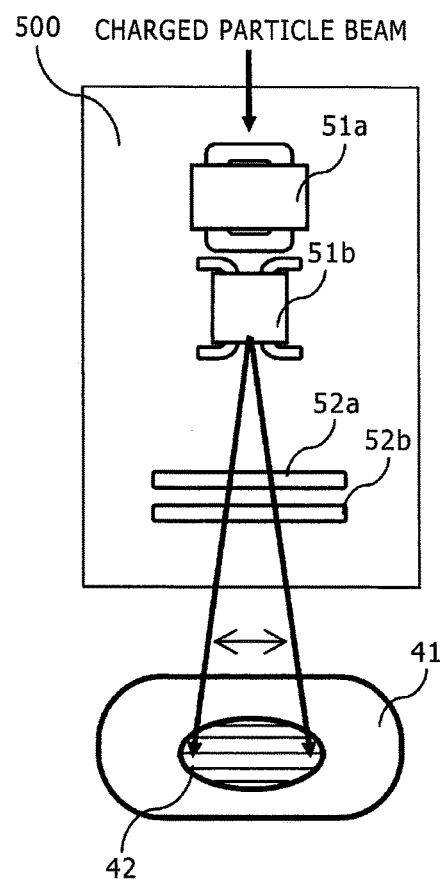
FIGS. 3A and 3B are schematic views showing a structure and the operating principle of an irradiation device (operating on the raster scanning method) used by the particle beam therapy system as the first embodiment of the invention, FIG. 3A being a front view of the structure, FIG. 3B being a plan view showing a charged particle beam applied to a tumor as seen from the upstream side.
Figure 3B:
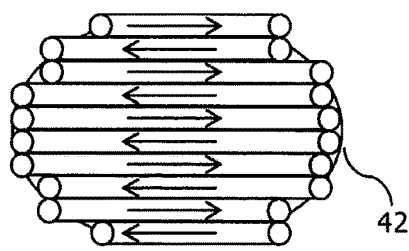

Explained next with reference to FIGS. 3A and 3B are the structure and the operating principle of the irradiation device 500 for use with the particle beam therapy system of this embodiment. FIG. 3A is a front view of the structure, and FIG. 3B is a plan view showing a charged particle beam applied to a tumor as seen from the upstream side. The irradiation device 500 operates on the raster scanning method, and includes scanning magnets 51 that cause the charged particle beam introduced by the beam transportation system 300 to be bent in the horizontal and vertical directions to scan a tumor 42 two-dimensionally in conformity to the cross-sectional shape of the tumor, and various beam monitors 52 that monitor the position, size (shape) and dose of the charged particle beam.

As shown in FIG. 3A, a three-dimensional shape of the tumor 42 of the patient 41 is divided into a plurality of layers in the depth direction according to a treatment plan. Each of the layers is then irradiated selectively using the extracted beam from the synchrotron while the energy level of the extracted beam is changed for irradiation. As shown in FIG. 3B, each layer is continuously scanned two-dimensionally with an irradiation beam using the scanning magnets 51 so that each area of the tumor to be irradiated is given a predetermined uniform dose distribution.

What follows is a detailed explanation of the operation sequence and time changes in operation parameters in effect during the extraction phase of the synchrotron in the particle beam therapy system of this embodiment. FIGS. 4A through 4H are explanation drawings for explaining this embodiment, and FIGS. 7A through 7G are explanation drawings for explaining the prior art. In the ensuing description, the operation sequence of this embodiment will be compared with that of the prior art and the differences therebetween will be explained.

FIGS. 4A through 4H and FIGS. 7A through 7G detail the extraction phase explained above in reference to FIGS. 2A through 2E. In each of FIGS. 4A through 4C and 4E as well as FIGS. 7A through 7C and 7E, the horizontal axis denotes time t and the vertical axis is the same as that in FIGS. 2A through 2C and 2E explained above. Meanwhile, in FIGS. 4D and 7D, the vertical axis represents the size of the stable area (i.e., of the triangle SA in FIGS. 8A through 8C) inside the stability limit. The vertical axis in FIGS. 4F and 7F denotes the excitation current of the beam extracted from the synchrotron 200 to the beam transportation system 300. The vertical axis in FIG. 4G represents the on/off state of the excitation current supplied from the excitation power supply 33A to the beam shielding magnet 33 in response to the command signal transmitted from the control apparatus 600 to the beam shielding magnet 33. The vertical axis in FIGS. 4H and 7G denotes the current of the irradiation beam applied from the irradiation device 500 to the tumor 42 of the patient 41.

FIGS. 4A through 4H and FIGS. 7A through 7G indicate an extraction segment 1, an extraction segment 2 and an extraction segment 3 of the extraction phase in which the charged particle beam is extracted from the synchrotron for irradiation to the tumor at energy levels E1, E2 and E3, respectively, in ascending order of energy level. In energy changing segments of the extraction phase, the charged particle beam orbiting in the synchrotron is accelerated additionally in energy from E1 to E2 and from E2 to E3. When the orbiting beam is to be additionally accelerated in the energy changing segments, as during the acceleration phase explained in FIGS. 2A through 2E, the control apparatus 600 performs control to increase the excitation currents of the bending magnets and quadrupole electromagnet to raise the frequency of the rf voltage (acceleration frequency) applied to the accelerating cavity. In the energy changing segments, it is mandatory to minimize the current of the extracted beam from the synchrotron to suppress the irradiation beam current so that the tumor will not be irradiated with a charged particle beam at a level other than the energy levels (E1, E2, E2) required for treatment.

With the prior art, as shown in FIG. 7B, the excitation current of the quadrupole electromagnet is adjusted before additional acceleration so as to enlarge the size of the stability limit (i.e., size of the stable area) as indicated in FIG. 7D and thereby to deviate from the operating conditions optimal for extraction. This is called the cancellation of the extraction conditions. Upon completion of additional acceleration, the excitation current of the quadrupole electromagnet is again adjusted to reduce the size of the stability limit (size of the stable area), thereby attaining again the operating conditions optimal for extraction. This is called the resetting of the extraction conditions. In terms of topological space shown in FIGS. 8A through 8C regarding beam extraction, a state transition occurs from FIG. 8A to FIG. 8B upon cancellation of the extraction conditions, and another state transition occurs from FIG. 8C to FIG. 8B upon resetting of the extraction conditions. In this case, FIG. 8B shows a topological space in effect when the size of the stability limit is kept optimal for beam extraction, and FIG. 8C indicates a topological space in effect when the size of the stability limit is enlarged upon energy level change during the extraction phase in order to suppress beam extraction.

With the prior art, as explained above, the excitation current of the quadrupole electromagnet is adjusted to enlarge the size of the stability limit (size of the stable area) so as to suppress beam extraction from the synchrotron in the energy changing segments. However, this method poses the problem of prolonging the time required to change energy levels because of the slow response speed of the quadrupole electromagnet having large inductance values. That is, in the operation sequence of FIGS. 7A through 7G, it takes longer to cancel and reset the extraction conditions, which entails the problem of having to prolong the energy changing segments.

With this embodiment, by contrast, the control apparatus 600 controls the excitation current of the quadrupole electromagnet in a manner keeping the size of the stability limit (size of the stable area) constant during the extraction phase as indicated by solid lines in FIGS. 4B and 4D; no adjustments are made to cancel or reset the extraction conditions (the state of FIG. 8B is maintained in the topological space). In the energy changing segments, as shown in FIG. 4E, the control apparatus 600 performs control to turn off (stop) the rf voltage (extraction rf voltage) applied to the extraction device 26 in the energy changing segments, whereby the number of particles extracted beyond the stability limit held constant is minimized. Ideally, this would sufficiently suppress the extracted beam current in the energy changing segments. In practice, however, the inventors with their experience with synchrotrons have found that, as shown by solid lines in FIG. 4F, there occurs an extracted beam current on a level not tolerated with the scanning irradiation method in the energy changing segments due to such disturbances as excitation current ripple of the magnets, an unstable orbiting beam, and scattering residual gas. There obviously is a method by which the control apparatus 600 adjusts the excitation currents of the quadrupole electromagnet and sextuple electromagnet constituting the synchrotron so as to slightly enlarge the size of the stability limit (size of the stable area) in the energy changing segments. This, however, prolongs the energy changing time that much. With this embodiment, as shown in FIG. 4G, the beam shielding magnet installed in the beam transportation system is excited to bend and discard the unnecessary charged particle beam extracted from the synchrotron in the energy changing segments, whereby an ideal irradiation beam current depicted in FIG. 4H is realized.

With this embodiment, it has been explained that the orbiting beam is accelerated successively in steps during the extraction phase of the synchrotron so as to extract the charged particle beam at a plurality of energy levels during that phase. Alternatively, as one way of operating the synchrotron, the charged particle beam injected from the pre-accelerator may be accelerated to a maximum energy level during the acceleration phase so that during the extraction phase, the charged particle beam is extracted in a stepped, successively decelerating manner at a plurality of energy levels. As another alternative, the charged particle beam may be extracted at a plurality of energy levels in a desired combination of acceleration and deceleration during the extraction phase of the synchrotron.

The irradiation device of this embodiment adopts the raster scanning method whereby the irradiation beam is continuously activated during movement between irradiation spots of the patient. Alternatively, the spot scanning method may be adopted whereby the irradiation beam is deactivated during movement between irradiation spots, and this method still provides the same effects as those of the raster scanning method.

According to this embodiment, where the orbiting beam is successively accelerated or decelerated during the extraction phase in order to change beam energy levels, there is no need to enlarge or reduce the size of the stability limit under control of the magnets of the synchrotron with the control apparatus 600 suppressing the unnecessary charged particle bean extracted from the synchrotron. This makes it possible to shorten the time required to change energy levels, improve dose rates, and shorten therapeutic irradiation time with the scanning method.

Also with this embodiment, the control apparatus of the particle beam therapy system keeps the size of the stability limit substantially constant during the extraction phase of the synchrotron and turns off (stops) the extraction rf voltage applied to the extraction device upon acceleration or deceleration for energy level change, which reduces the unnecessary charged particle beam extracted from the synchrotron. That in turn reduces the charged particle beam to be discarded in the beam transportation system and improves the efficiency in charged particle beam utilization, thereby improving dose rates and shortening therapeutic irradiation time with the scanning method.

Further with this embodiment, there is no need to equip the synchrotron acceleration with dedicated magnets having low inductance values and operating at high speed, so that the system is kept from getting large in size and higher in cost.

Second Embodiment

The configuration and the operation of a particle beam therapy system as the second embodiment of the present invention are now explained. The overall configuration of the particle beam therapy system as the second embodiment is the same as that of the first embodiment in FIG. 1. The operation sequence of the synchrotron is the same as that of the first embodiment in FIGS. 2A through 2E except for during the extraction phase. Also, the structure and the operating principle of the irradiation device are the same as those of the first embodiment in FIGS. 3A and 3B. Explained below are some differences in the operation sequence during the extraction phase of the synchrotron between the first embodiment and the second embodiment.

In FIGS. 4A through 4H showing a detailed operation sequence and time changes in operation parameters during the extraction phase of the synchrotron, broken lines correspond to the second embodiment and are indicative of the differences from the first embodiment. With the second embodiment, as indicated by broken lines in FIGS. 4C and 4D, the control apparatus 600 controls the frequency of the rf voltage (acceleration frequency) applied to the accelerating cavity in the energy changing segments in order to enlarge the size of the stability limit (size of the stable area). In terms of topological space shown in FIGS. 8A through 8C regarding beam extraction, a state transition occurs from FIG. 8B to FIG. 8c at the start of an energy changing segment, and another state transition occurs from FIG. 8C to FIG. 8B at the end of the energy changing segment. In this case, as indicated by broken lines in FIG. 4F, the current of the extracted beam from the synchrotron is suppressed in the energy changing segments.

With the excitation currents of the bending magnets and quadrupole electromagnet held constant, controlling only the acceleration frequency provides two effects: changing the energy level of the orbiting beam, and varying the position of the orbit. Changing the energy level of the orbiting beam affects the convergent force on the orbiting beam in the horizontal and vertical directions, which amounts to the same effect as adjusting the excitation current of the quadrupole electromagnet. Varying the position of the orbit involves causing the orbit to deviate from the center position of the sextuple electromagnet and thereby affects the convergent force on the orbiting beam in the horizontal and vertical directions, which also amounts to the same effect as adjusting the excitation current of the quadrupole electromagnet. Suitably combining these two effects makes it possible efficiently to control the size of the stability limit (size of the stable area). On the other hand, acceleration frequency can be controlled at high speed so that it is fully possible thereby to control the convergent force on the orbiting beam on a time scale of about 1 ms.

According to the second embodiment, where the orbiting beam is to be successively accelerated or decelerated during the extraction phase of the synchrotron, the control apparatus 600 controls the acceleration frequency of the synchrotron to enlarge the size of the stability limit and thereby to suppress extraction of the unnecessary charged particle beam. This makes it possible to suppress the charged particle beam to be discarded in the beam transportation system, improve the efficiency in charged particle beam utilization, and enhance dose rates so that therapeutic irradiation time with the scanning method can be shortened.

Also with the second embodiment, the acceleration frequency that can be controlled at high speed need only be controlled for the purpose. There is no need to equip the synchrotron acceleration with dedicated magnets having low inductance values and operating at high speed, so that the system is kept from getting large in size and higher in cost.

Third Embodiment

Figure 5:
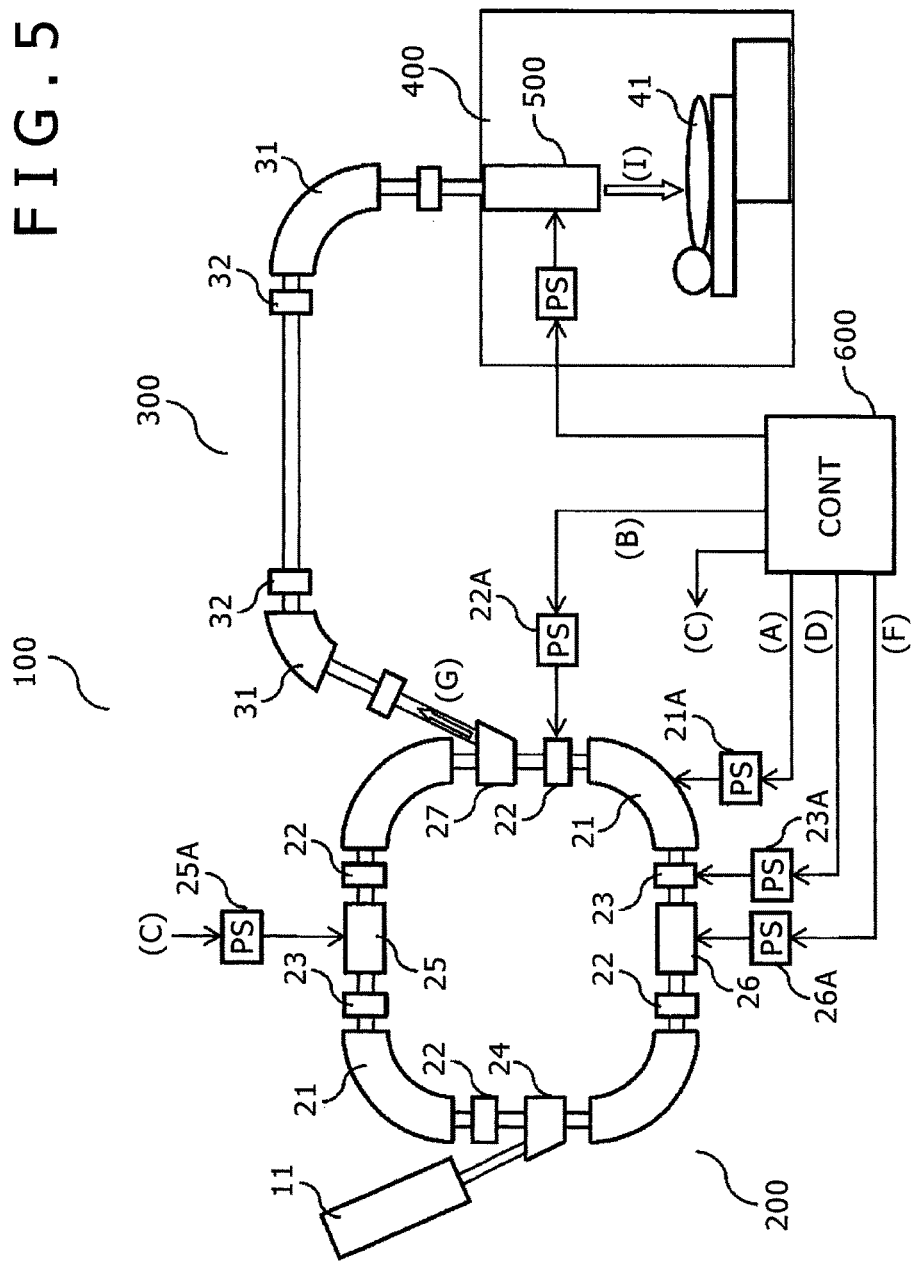
FIG. 5 is a schematic view showing a configuration of a particle beam therapy system as a third embodiment of the present invention.

The configuration and the operation of a particle beam therapy system as the third embodiment of the present invention are now explained. An overall configuration of the particle beam therapy system as the third embodiment is shown in FIG. 5, and a detailed operation sequence and time changes in operation parameters during the extraction phase of the synchrotron are depicted in FIGS. 6A through 6G. Below is an explanation of only the differences between the third embodiment on the one hand and the first and the second embodiments on the other hand.

As with the second embodiment, the third embodiment involves controlling the frequency of the rf voltage (acceleration frequency) applied to the accelerating cavity in the energy changing segments so as to enlarge the size of the stability limit (size of the stable area), as shown in FIGS. 6C and 6D. This makes it possible to fully suppress the current of the extracted beam from the synchrotron in the energy changing segments as depicted in FIG. 6F. In this case, an ideal irradiation beam current shown in FIG. 6G can be realized without discarding the unnecessary extracted beam using the beam shielding magnet in the beam transportation system. For this reason, the beam transportation system in FIG. 5 is not furnished with the beam shielding magnet and its excitation power supply.

According to the third embodiment, where the orbiting beam is to be successively accelerated or decelerated during the extraction phase of the synchrotron, the control apparatus 600 controls the acceleration frequency of the synchrotron to enlarge the size of the stability limit and thereby to fully suppress extraction of the unnecessary charged particle beam. Thus there is no need to equip the beam transportation system with functionality to block the extracted beam, which keeps the system simple in structure and low in cost.

In addition to particle beam therapy systems designed primarily for cancer treatment, the present invention can also be applied to research areas in physics where a target needs to be irradiated with a charged particle beam accelerated by a synchrotron to a high energy level in a desired intensity distribution pattern with high accuracy.

As many apparently different embodiments of this invention may be made without departing from the spirit and scope thereof, it is to be understood that the invention is not limited to the specific embodiments thereof except as defined in the appended claims.

What is claimed is:

1. A particle beam therapy system comprising:
a synchrotron which accelerates a charged particle beam injected from a pre-accelerator up to a predetermined energy level at least equal to a minimum particle beam energy level required to irradiate a patient in a treatment room during an extraction phase of aid charged particle beam before applying a high-frequency voltage to an extraction device to extract the charged particle beam caused to exceed a stability limit during a first extraction segment of a plurality of successive extraction segments of extraction of said charged particle beam during said extraction phase of said charged particle beam;
a beam transportation system which transports the charged particle beam extracted from the synchrotron to a treatment room in each of said successive extraction segments during said extraction phase, and
an irradiation device which irradiates the patient in the treatment room with the charged particle beam in conformity to the tumor shape of the patient in each of the successive extraction segments during said extraction phase;
wherein the synchrotron has functionality to accelerate or decelerate the charged particle beam successively to extract the charged particle beam at a plurality of energy levels during each extraction segment of the synchrotron during the irradiating of the patient in the treatment room during said extraction phase, while maintaining the particle beam energy level at least at said required minimum particle beam energy level during acceleration or declaration of the charged particle beam between the successive ones of the extraction segments during said extraction phase, the beam transportation system further having functionality to block off an unnecessary charged particle beam extracted from the synchrotron during acceleration or deceleration.

2. The particle beam therapy system according to claim 1, wherein, during each of the extraction segments of said extraction phase of the synchrotron during which the synchrotron extracts the charged particle beam at a selected one of the plurality of energy levels by successively accelerating or decelerating the charged particle beam, magnets constituting part of the synchrotron are controlled to maintain the stability limit substantially constant in size, and wherein the high-frequency voltage applied to the extraction device is turned off during acceleration or deceleration.

3. The particle beam therapy system according to claim 1, wherein, upon acceleration or deceleration of the charged particle beam during each of the extraction segments of said extraction phase of the synchrotron, the synchrotron suppresses the extraction of the unnecessary charged particle beam by having an acceleration frequency controlled to enlarge the stability limit in size.

4. A particle beam therapy system comprising:
- a synchrotron which accelerates a charged particle beam injected from a pre-accelerator up to a predetermined energy level at least equal to a minimum particle beam energy level required to irradiate a patient in a treatment room during an extraction phase of said charged particle beam before applying a high-frequency voltage to an extraction device to extract the charged particle beam caused to exceed a stability limit during a first extraction segment of a plurality of successive extraction segments of extraction of said charged particle beam during said extraction phase of said charged particle beam;
- a beam transportation system which transports the charged particle beam extracted from the synchrotron to a treatment room in each of said successive extraction segments during said extraction phase, and
- an irradiation device which irradiates the patient in the treatment room with the charged particle beam in conformity to the tumor shape of the patient in each of the successive extraction segments during said extraction phase;

wherein the synchrotron has functionality to accelerate or decelerate the charged particle beam successively to extract the charged particle beam at a plurality of energy levels during each extraction segment of the synchrotron during the irradiating of the patient in the treatment room during said extraction phase, while maintaining the particle beam energy level at least at said required minimum particle beam energy level during acceleration or deceleration of the charged particle beam between the successive ones of the extraction segments during said extraction phase, the synchrotron further having functionality to suppress the extraction of an unnecessary charged particle beam by having an acceleration frequency controlled to enlarge the stability limit in size during acceleration or deceleration.

* * * * *